US008897893B2

(12) United States Patent
Pianca

(10) Patent No.: US 8,897,893 B2
(45) Date of Patent: *Nov. 25, 2014

(54) SYSTEMS AND METHODS FOR PROVIDING ELECTRICAL STIMULATION OF MULTIPLE DORSAL ROOT GANGLIA WITH A SINGLE LEAD

(71) Applicant: Boston Scientific Neuromodulation Corporation, Valencia, CA (US)

(72) Inventor: Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/222,496

(22) Filed: Mar. 21, 2014

(65) Prior Publication Data

US 2014/0207148 A1     Jul. 24, 2014

Related U.S. Application Data

(63) Continuation of application No. 13/901,158, filed on May 23, 2013, now Pat. No. 8,718,790.

(60) Provisional application No. 61/651,917, filed on May 25, 2012.

(51) Int. Cl.
  *A61N 1/00* (2006.01)
  *A61N 1/05* (2006.01)
  *A61N 1/36* (2006.01)

(52) U.S. Cl.
  CPC ............ *A61N 1/0558* (2013.01); *A61N 1/0551* (2013.01); *A61N 1/36185* (2013.01)
  USPC .......................................................... 607/117

(58) Field of Classification Search
  USPC .......................................................... 607/117
  See application file for complete search history.

(56) References Cited

U.S. PATENT DOCUMENTS

| 3,918,440 A | 11/1975 | Kraus |
| 5,330,477 A | 7/1994 | Crook |
| 5,738,521 A | 4/1998 | Dugot |

(Continued)

FOREIGN PATENT DOCUMENTS

| AU | 2012201634 A1 | 4/2012 |
| WO | 03020365 A1 | 3/2003 |

(Continued)

*Primary Examiner* — Robert N Wieland
(74) *Attorney, Agent, or Firm* — Lowe Graham Jones PLLC; Bruce E. Black

(57) ABSTRACT

A method for implanting an electrical stimulation lead into a patient includes advancing a distal end of a multi-armed lead into an epidural space of the patient. The multi-armed lead includes first and second stimulation arms extending from a main body portion. The first stimulation arm is guided into and through a first intervertebral foramen. The first stimulation arm is positioned in proximity to a first dorsal root ganglion. The first stimulation aim is positioned with electrodes disposed along the first stimulation arm in operational proximity to the first dorsal root ganglion. The second stimulation arm is guided into and through a second intervertebral foramen. The second stimulation arm is positioned in proximity to a second dorsal root ganglion. The second stimulation arm is positioned with electrodes disposed along the second stimulation arm in operational proximity to the second dorsal root ganglion.

20 Claims, 10 Drawing Sheets

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2005/0033374 A1 | 2/2005 | Gerber |
| 2007/0150036 A1 | 6/2007 | Anderson |
| 2008/0140169 A1 | 6/2008 | Imran |
| 2010/0241179 A1 * | 9/2010 | Gielen et al. .............. 607/2 |
| 2013/0317583 A1 | 11/2013 | Pianca |
| 2013/0317585 A1 | 11/2013 | Barker |
| 2013/0317586 A1 | 11/2013 | Pianca |
| 2013/0317587 A1 | 11/2013 | Barker |
| 2013/0317588 A1 | 11/2013 | Howard et al. |

FOREIGN PATENT DOCUMENTS

| | | |
|---|---|---|
| WO | 03084398 A1 | 10/2003 |
| WO | 2005120203 A2 | 12/2005 |
| WO | 2006029257 A2 | 3/2006 |
| WO | 2007041604 A2 | 4/2007 |
| WO | 2010083308 A1 | 7/2010 |

* cited by examiner

US 8,897,893 B2

SYSTEMS AND METHODS FOR PROVIDING ELECTRICAL STIMULATION OF MULTIPLE DORSAL ROOT GANGLIA WITH A SINGLE LEAD

CROSS-REFERENCE TO RELATED APPLICATIONS

This application claims is a continuation of U.S. application Ser. No. 13/901,158 filed May 23, 2013, now U.S. Pat. No. 8,718,790, which claims the benefit under 35 U.S.C. §119(e) of U.S. Provisional Patent Application Ser. No. 61/651,917 filed on May 25, 2012, which is incorporated herein by reference.

FIELD

The present invention is directed to the area of implantable electrical stimulation systems and methods of making and using the systems. The present invention is also directed to implantable electrical stimulation leads configured and arranged for simultaneously stimulating two or more dorsal root ganglia with a single lead, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Dorsal root ganglia are nodules of cell bodies disposed along the dorsal roots of spinal nerves. Dorsal root ganglia are disposed external to the epidural space. Dorsal root ganglia, however, are disposed in proximity to the spinal cord and the vertebral column.

BRIEF SUMMARY

In one embodiment, a method for implanting an electrical stimulation lead into a patient includes advancing a distal end of a multi-armed lead into an epidural space of the patient. The multi-armed lead includes a main body portion, a first stimulation arm extending from a distal end of the main body portion, and a second stimulation arm extending from the distal end of the main body portion. The first stimulation arm is guided into and through a first intervertebral foramen from inside the epidural space. The first stimulation arm is positioned in proximity to a first dorsal root ganglion that extends through the first intervertebral foramen. The first stimulation arm is positioned with a plurality of electrodes disposed along the first stimulation arm in operational proximity to the first dorsal root ganglion. The second stimulation arm is guided into and through a second intervertebral foramen from inside the epidural space. The second stimulation arm is positioned in proximity to a second dorsal root ganglion that extends through the second intervertebral foramen. The second stimulation arm is positioned with a plurality of electrodes disposed along the second stimulation arm in operational proximity to the second dorsal root ganglion.

In another embodiment, an implantable lead for providing electrical stimulation to a patient includes a lead body having a proximal end, a distal end, and a longitudinal length. The lead body includes a main body portion having a proximal end, a distal end, and a longitudinal length. A first stimulation arm extends from the distal end of the main body portion. The first stimulation arm has a radius of curvature. A plurality of electrodes are disposed along the first stimulation arm. A second stimulation arm extends from the distal end of the main body portion. The second stimulation arm has a radius of curvature. A plurality of electrodes are disposed along the second stimulation arm. A plurality of terminals are disposed at the proximal end of the main body portion. A plurality of conductors electrically couple the plurality of terminals to the plurality of electrodes. At least one of the plurality of conductors electrically couples at least one terminal of the plurality of terminals to at least one electrode of the plurality of electrodes disposed along the first stimulation aim. At least one of the plurality of conductors electrically couples at least one terminal of the plurality of terminals to at least one electrode of the plurality of electrodes disposed along the second stimulation arm.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads configured and arranged for anchoring to one or more bony structures in proximity to a target stimulation region, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; 8,224,450; and 8,364,278; and U.S. Patent Application Publication No. 2007/0150036, all of which are incorporated by reference.

Figure 1:
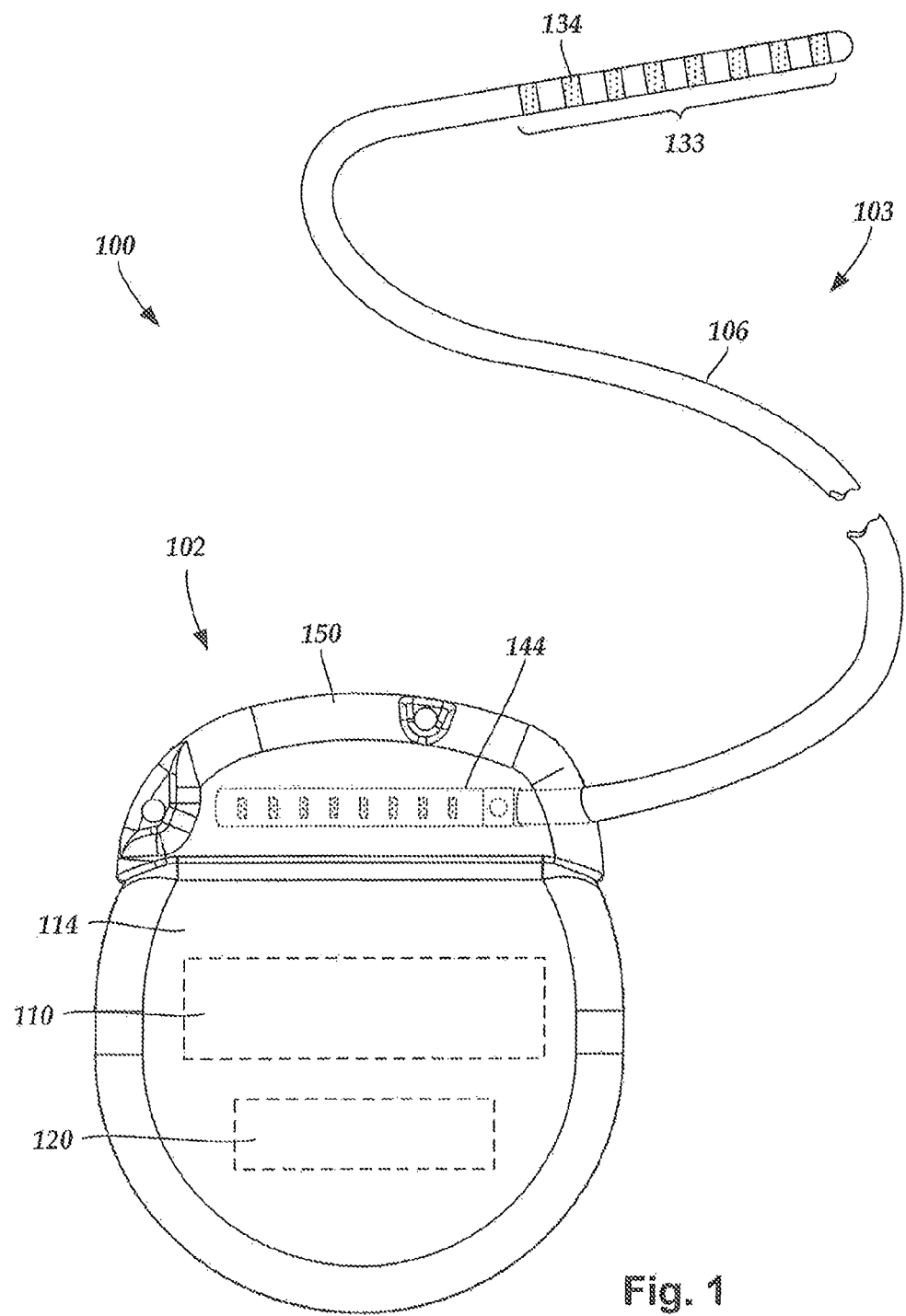
FIG. 1 is a schematic view of another embodiment of an electrical stimulation system that includes a percutaneous lead body coupled to a control module, according to the invention.

FIG. 1 illustrates schematically one embodiment of an electrical stimulation system 100. The electrical stimulation system 100 includes a control module (e.g., a stimulator or pulse generator) 102 and a percutaneous lead 103. The lead 103 includes a plurality of electrodes 134 that form an array of electrodes 133. The control module 102 typically includes an electronic subassembly 110 and an optional power source 120 disposed in a sealed housing 114. The lead 103 includes a lead body 106 coupling the control module 102 to the plurality of electrodes 134. In at least some embodiments, the lead body 106 is isodiametric.

The control module 102 typically includes one or more connector assemblies 144 into which the proximal end of the lead body 106 can be plugged to make an electrical connection via connector contacts (e.g., 216 in FIG. 2A) disposed in the connector assembly 144 and terminals (e.g., 210 in FIG. 2A) disposed along the lead body 106. The connector contacts are coupled to the electronic subassembly 110 and the terminals are coupled to the electrodes 134. Optionally, the control module 102 may include a plurality of connector assemblies 144.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 224 (see FIG. 2C) can be disposed between the lead body 106 and the control module 102 to extend the distance between the lead body 106 and the control module 102.

The electrical stimulation system or components of the electrical stimulation system, including the lead body 106 and the control module 102, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the lead body 106 are typically disposed in, or separated by, a non-conductive, biocompatible material including, for example, silicone, polyurethane, and the like or combinations thereof. The lead body 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead body 106 to the proximal end of the lead body 106.

Terminals (e.g., 210 in FIG. 2A) are typically disposed at the proximal end of the lead body 106 for connection to corresponding conductive contacts (e.g., 216 in FIG. 2A) in one or more connector assemblies (e.g., 144 in FIG. 1) disposed on, for example, the control module 102 (or to other devices, such as conductive contacts on a lead extension, an operating room cable, a splitter, an adaptor, or the like).

Conductive wires (see e.g., 508 of FIG. 5B) extend from the plurality of terminals (see e.g., 210 in FIG. 2A) to the plurality of electrodes 133. Typically, each of the plurality of terminals is electrically coupled to at least one of the plurality of electrodes 133. In some embodiments, each of the plurality of terminals is coupled to a single electrode 134 of the plurality of electrodes 133.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the lead 103. The one or more lumens may, optionally, be flushed continually, or on a regular basis, with saline, epidural fluid, or the like. The one or more lumens can be permanently or removably sealable at the distal end.

As discussed above, the lead body 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, the lead body 106 includes eight terminals that are shown coupled with eight conductive contacts disposed in the connector assembly 144.

Figure 2A:
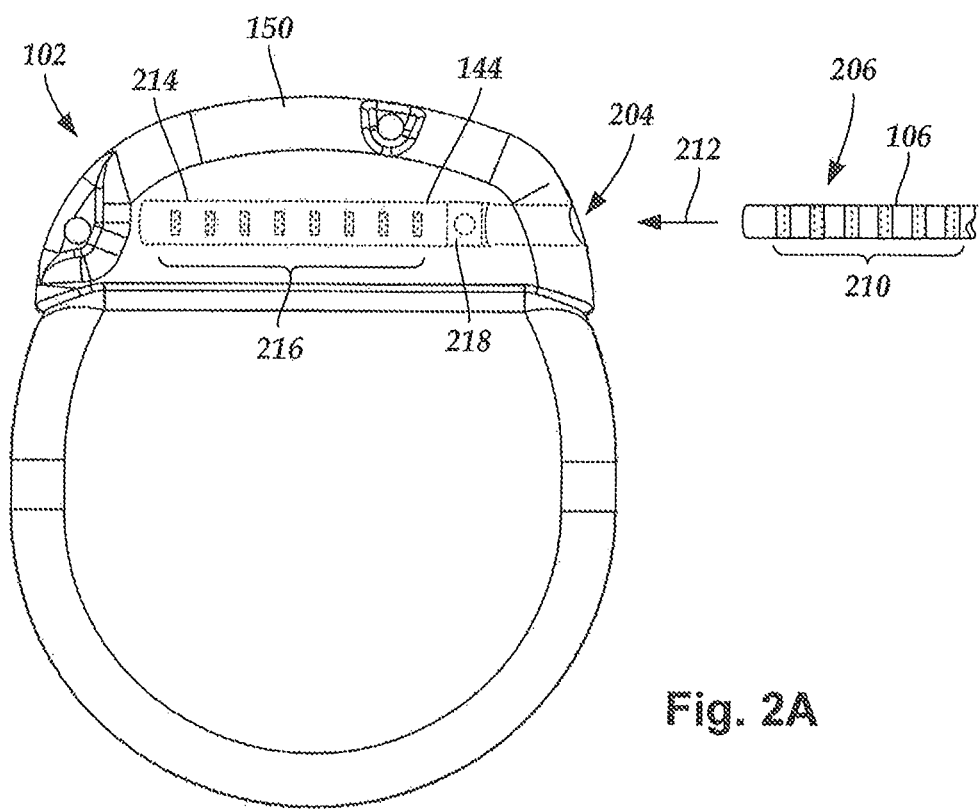
FIG. 2A is a schematic view of one embodiment of a plurality of connector assemblies disposed in the control module of FIG. 1, the connector assemblies configured and arranged to receive the proximal portions of the lead bodies of FIG. 1, according to the invention.

FIG. 2A is a schematic side view of one embodiment of a connector assembly 144 disposed on the control module 102. In FIG. 2A, the proximal end 306 of the lead body 106 is shown configured and arranged for insertion to the control module 102.

In FIG. 2A, the connector assembly 144 is disposed in the header 150. In at least some embodiments, the header 150 defines a port 204 into which the proximal end 206 of the lead body 106 with terminals 210 can be inserted, as shown by directional arrows 212, in order to gain access to the connector contacts disposed in the connector assembly 144.

The connector assembly 144 includes a connector housing 214 and a plurality of connector contacts 216 disposed therein. Typically, the connector housing 214 defines a port (not shown) that provides access to the plurality of connector contacts 216. In at least some embodiments, the connector assembly 144 further includes a retaining element 218 configured and arranged to fasten the corresponding lead body 106 to the connector assembly 144 when the lead body 106 is inserted into the connector assembly 144 to prevent undesired detachment of the lead body 106 from the connector assembly 144. For example, the retaining element 218 may include an aperture 220 through which a fastener (e.g., a set screw, pin, or the like) may be inserted and secured against an inserted lead body 106.

When the lead body 106 is inserted into the port 204, the connector contacts 216 can be aligned with the terminals 210 disposed on the lead body 106 to electrically couple the control module 102 to the electrodes (134 of FIG. 1) disposed at a distal end of the lead body 106. Examples of connector assemblies in control modules are found in, for example, U.S. Pat. Nos. 7,244,150 and 8,224,450, which are incorporated by reference.

Figure 2B:
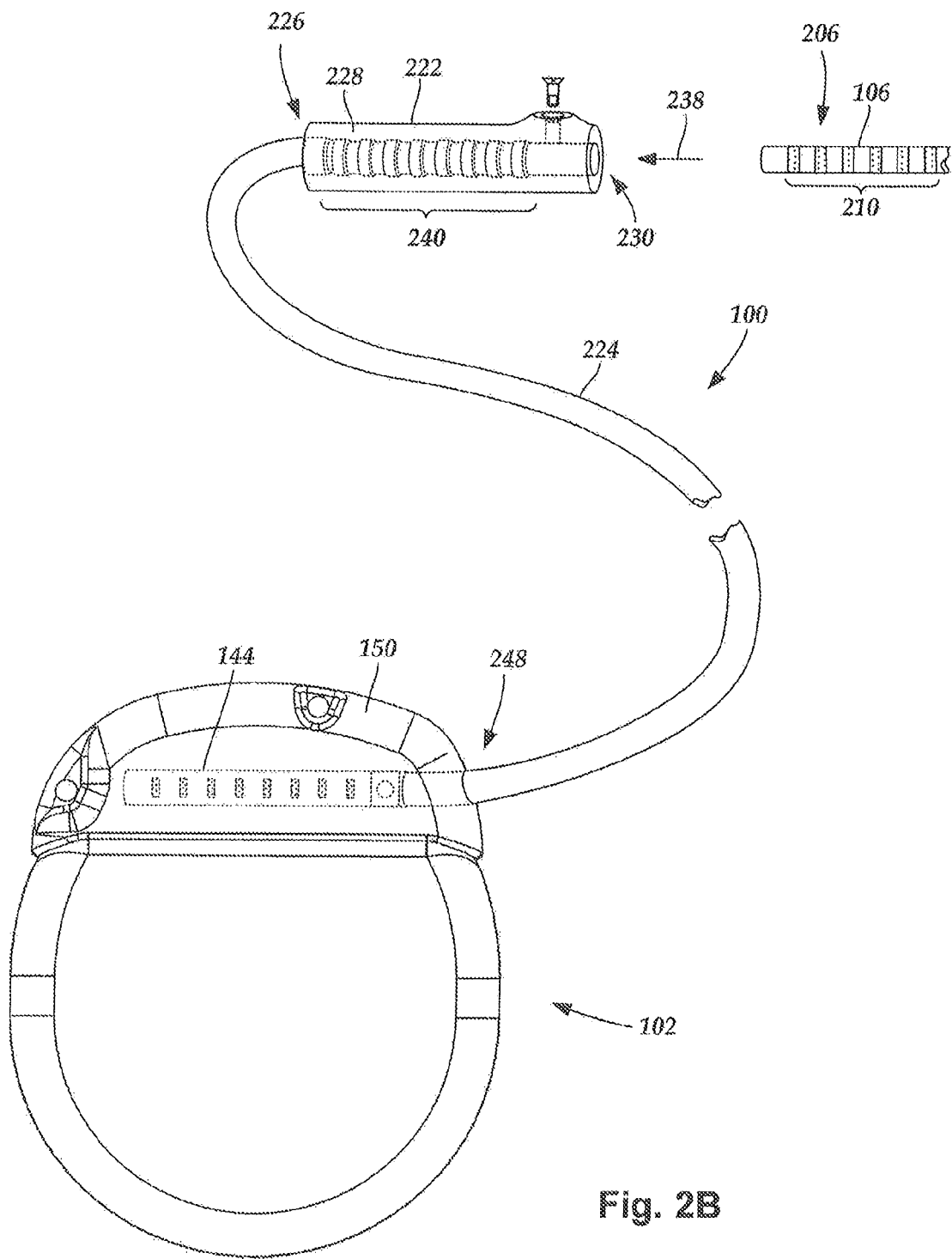
FIG. 2B is a schematic view of one embodiment of a proximal portion of the lead body of FIG. 1, a lead extension, and the control module of FIG. 1, the lead extension configured and arranged to couple the lead body to the control module, according to the invention.

In at least some embodiments, the electrical stimulation system includes one or more lead extensions. The lead body 106 can be coupled to one or more lead extensions which, in turn, are coupled to the control module 102. In FIG. 2B, a lead extension connector assembly 222 is disposed on a lead extension 224. The lead extension connector assembly 222 is shown disposed at a distal end 226 of the lead extension 224. The lead extension connector assembly 222 includes a contact housing 228. The contact housing 228 defines at least one port 230 into which a proximal end 206 of the lead body 106 with terminals 210 can be inserted, as shown by directional arrow 238. The lead extension connector assembly 222 also includes a plurality of connector contacts 240. When the lead body 106 is inserted into the port 230, the connector contacts 240 disposed in the contact housing 228 can be aligned with the terminals 210 on the lead body 106 to electrically couple the lead extension 224 to the electrodes (134 of FIG. 1) disposed at a distal end (not shown) of the lead body 106.

The proximal end of a lead extension can be similarly configured and arranged as a proximal end of a lead body. The lead extension 224 may include a plurality of conductive wires (not shown) that electrically couple the connector contacts 240 to terminal on a proximal end 248 of the lead extension 224. The conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a lead extension connector assembly disposed in another lead extension. In other embodiments (as shown in FIG. 2B), the proximal end 248 of the lead extension 224 is configured and arranged for insertion into the connector assembly 144 disposed on the control module 102.

Figure 3A:
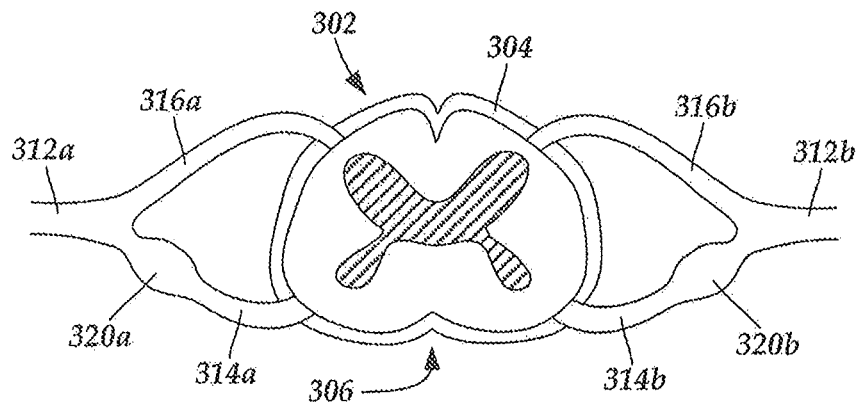
FIG. 3A is a schematic transverse cross-sectional view of spinal nerves extending from a spinal cord, the spinal nerves including dorsal root ganglia.

Turning to FIG. 3A, in at least some embodiments one or more dorsal root ganglia ("DRG") are potential target stimulation locations. FIG. 3A schematically illustrates a transverse cross-sectional view of a spinal cord 302 surrounded by dura 304. The spinal cord 302 includes a midline 306 and a plurality of levels from which spinal nerves 312a and 312b extend. In at least some spinal cord levels, the spinal nerves 312a and 312b extend bilaterally from the midline 306 of the spinal cord 302. In FIG. 3A, the spinal nerves 312a and 312b are shown attaching to the spinal cord 302 at a particular spinal cord level via corresponding dorsal roots 314a and 314b and corresponding ventral (or anterior) roots 316a and 316b. Typically, the dorsal roots 314a and 314b relay sensory information into the spinal cord 302 and the ventral roots 316a and 316b relay motor information outward from the spinal cord 302. The DRG 320a and 320b are nodules of cell bodies that are disposed along the dorsal roots 316a and 316b in proximity to the spinal cord 302.

Figure 3B:
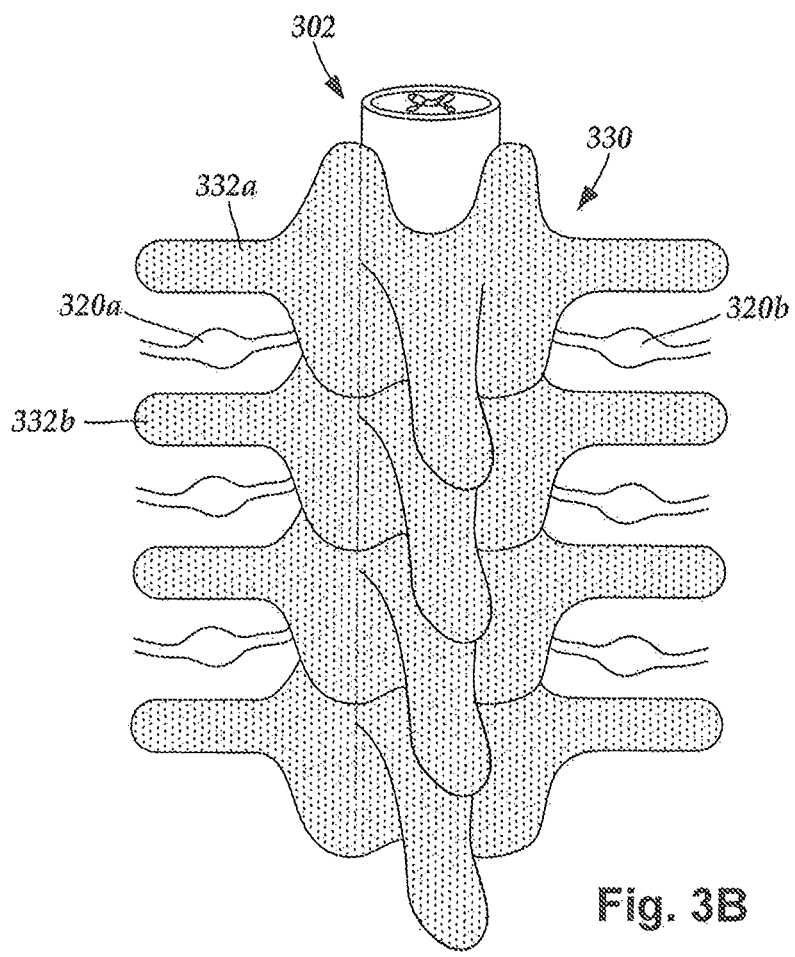
FIG. 3B is a schematic perspective view of a portion of the spinal cord of FIG. 3A disposed in a portion of a vertebral column with the dorsal root ganglia of FIG. 3A extending outward from the vertebral column.

FIG. 3B schematically illustrates a perspective view of a portion of the spinal cord 302 disposed along a portion of a vertebral column 330. The vertebral column 330 includes stacked vertebrae, such as vertebrae 332a and 332b, and a plurality of DRGs 320a and 320b extending outwardly bilaterally from the spinal cord 302 at different spinal cord levels.

Figure 3C:
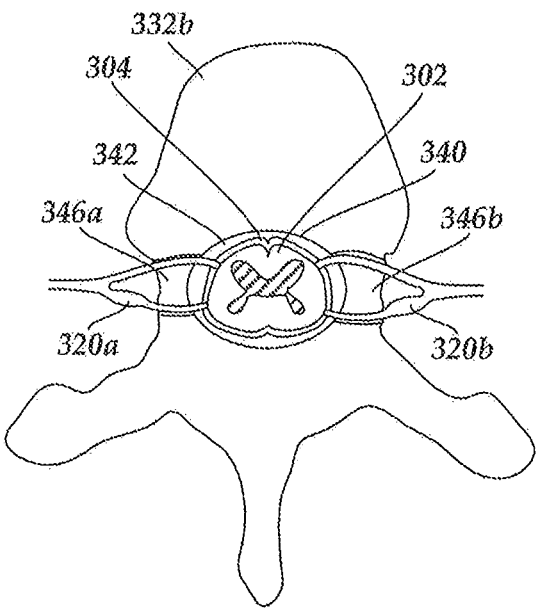
FIG. 3C is a schematic top view of a portion of the spinal cord of FIG. 3A disposed in a vertebral foramen defined in a vertebra of the vertebral column of FIG. 3B, the vertebra also defining intervertebral foramina extending between an outer surface of the vertebra and the vertebral foramen, the intervertebral foramina providing an opening through which the dorsal root ganglia of FIG. 3B can extend outward from the spinal cord of FIG. 3B.

FIG. 3C schematically illustrates a top view of a portion of the spinal cord 302 and surrounding dura 304 disposed in a vertebral foramen 340 defined in the vertebra 332b. The vertebrae, such as the vertebrae 332a and 332b, are stacked together and the vertebral foramina 340 of the vertebrae collectively form a spinal canal through which the spinal cord 302 extends. The space within the spinal canal between the dura 304 and the walls of the vertebral foramen 340 defines the epidural space 342. Intervertebral foramina 346a and 346b, defined bilaterally along sides of the vertebra 332b, form openings through the vertebra 332b between the epidural space 342 and the environment external to the vertebra 332b.

Figure 3D:
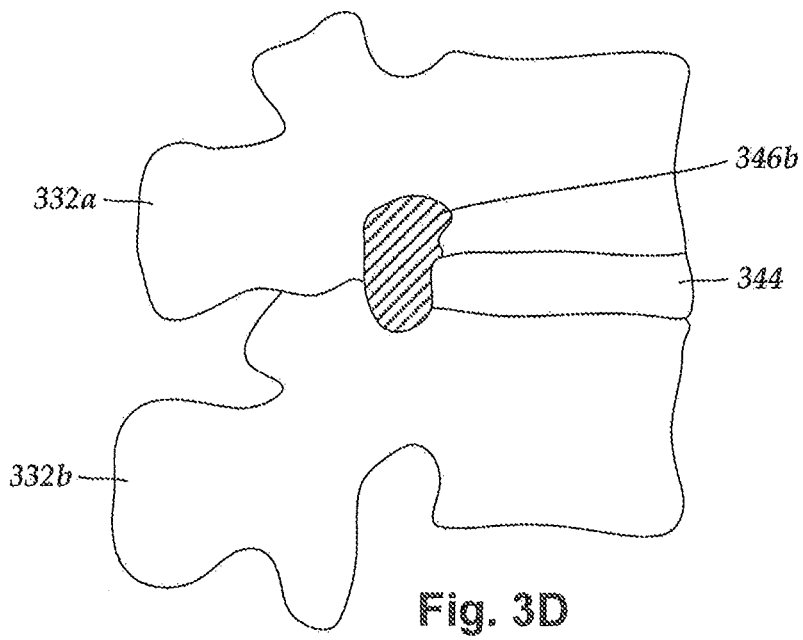
FIG. 3D is a schematic side view of two vertebrae of the vertebral column of FIG. 3B, the vertebrae defining an intervertebral foramen through which one of the dorsal root ganglia of FIG. 3B can extend outward from the spinal cord of FIG. 3B.

FIG. 3D schematically illustrates a side view of two vertebrae 332a and 332b coupled to one another by a disc 344. In FIG. 3D, the intervertebral foramen 346b is shown defined between the vertebrae 332a and 332b. The intervertebral foramen 346b provides an opening for one or more of the dorsal root 314b, ventral root 316b, and DRG 320b to extend outwardly from the spinal cord 302 to the environment external to the vertebrae 332a and 332b.

Figure 4:
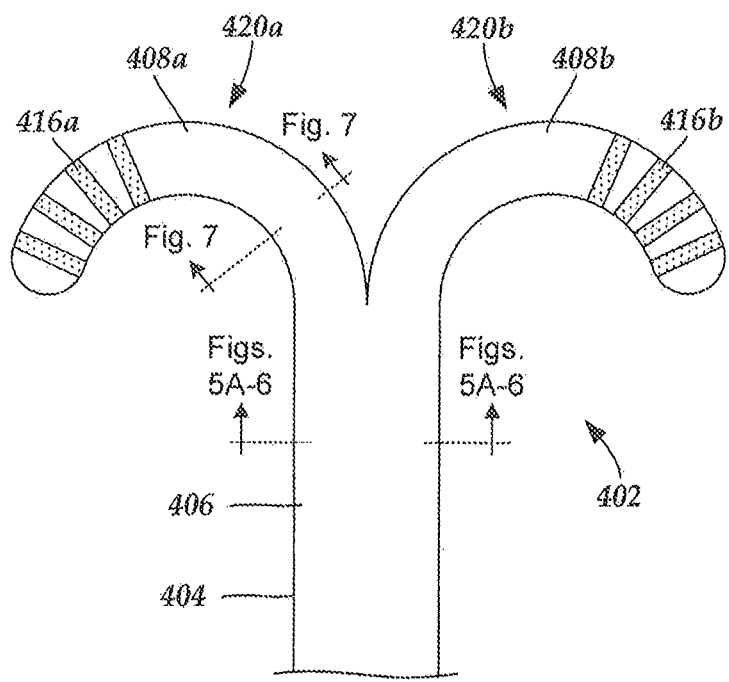
FIG. 4 is a schematic side view of one embodiment of a distal end of a multi-armed lead, the multi-armed lead including a body with two stimulation arms extending from a distal end of a major portion of the body; according to the invention.

Turning to FIG. 4, although the DRG are not within the epidural space, the DRG may be accessible to a lead from within the epidural space via the intervertebral foramina. In at least some embodiments, once the distal end of the lead is inserted into the epidural space the distal end of the lead can be advanced out of the epidural space through one of the intervertebral foramen, and positioned in proximity to the desired DRG.

In at least some instances, it is desirable to concurrently stimulate two or more DRG, such as both DRG located at a particular spinal cord level (e.g., the DRG 320a and 320b), or two or more DRG located on the same side of a vertebral column, or even two or more DRG at different spinal cord levels and on different sides of the vertebral column. In which case, separate conventional leads may be used to independently stimulate each DRG. Introducing two or more leads into the epidural space may require that each of the leads be separately introduced into the patient, thereby potentially increasing the time and complexity of an implantation procedure, and also potentially requiring the patient to undergo several different needle insertions. Introducing two or more leads into the epidural space may also be hindered due to size constraints within the epidural space.

As herein described, a multi-armed percutaneous lead includes a plurality of electrodes disposed on each of multiple distal arms. The multi-armed lead may be used to simultaneously stimulate two or more target stimulation regions, such as two or more different DRG, using a single lead. In at least some embodiments, the multi-armed lead may be used to perform simultaneous stimulation of each of two bilateral DRG (e.g., at a desired spinal level) using a single lead.

FIG. 4 is a schematic side view of one embodiment of a distal end of a multi-armed lead 402. The multi-armed lead 402 includes a body 404 with a major portion 406 and a plurality of stimulation arms 408a and 408b extending from the major portion 406. In FIG. 4, the plurality of stimulation arms 408a and 408b are shown extending from a distal end of the major portion 406. The multi-armed lead 402 can include any suitable number of stimulation mins 408a and 408b extending from the major portion 406. In FIG. 4, two stimulation arms 408a and 408b are shown. It will be understood that other numbers of stimulation arms 408a and 408b may be extended from the major portion 406 including, for example, three, four, five, six, seven, eight, or more stimulation arms 408a and 408b.

One or more electrodes, such as electrodes 416a and 416b, are disposed on each of the stimulation arms 408a and 408b, respectively. In FIG. 4, four electrodes are disposed on each of the stimulation arms 408a and 408b. It will be understood that any suitable number of electrodes may be disposed on each of the stimulation arms 408a and 408b including, for example, one, two, three, four, five, six, seven, eight, nine, ten, eleven, twelve, thirteen, fourteen, fifteen, sixteen, or more electrodes. In some embodiments, the same number of electrodes is disposed on each of the stimulation arms 408a and 408b. In other embodiments, a different number of electrodes are disposed on each of the stimulation arms 408a and 408b.

In at least some embodiments, the electrodes are configured as ring electrodes that extend completely around radii of curvature of the stimulation arms 408a and 408b. In at least some other embodiments, the electrodes are configured such that the electrodes extend around less than complete radii of curvature of the stimulation arms 408a and 408b. For example, the electrodes may be formed as segmented electrodes, cuff-shaped electrodes, arc-shaped electrodes, a tip electrode, or the like. It may be an advantage to form the electrodes such that, for each of the stimulation arms 408a and 408b, the electrodes extend around less than a complete radius of curvature of the stimulation arm so that energy propagated from the electrodes can be directed primarily in the direction of the target stimulation location.

A plurality of terminals (see e.g., terminals 210 of FIGS. 2A-2B) are disposed at a proximal end of the lead body 404. In at least some embodiments, the number of terminals is equal to the collective number of electrodes disposed on each of the stimulation arms 408a and 408b. A plurality of elongated conductors (508 in FIG. 5B) electrically couples the terminals to the electrodes.

In at least some embodiments, the stimulation arms 408a and 408b each include at least one bend 420a and 420b, respectively. In at least some embodiments, the stimulation arms 408a and 408b each include exactly one bend 420a and 420b, respectively. In at least some embodiments, the at least one bends 420a and 420b are configured and arranged to extend their respective stimulation arms 408a and 408b in opposite directions from one another. In at least some embodiments, the at least one bend 420a and the at least one bend 420b are symmetrical with one another along an axis extending along a longitudinal length of a distal end of the major portion 406 of the lead body 404.

In at least some embodiments, the at least one bend 420a and the at least one bend 420b are pre-defined in their respective stimulation arms (e.g., the bends 420a and 420b are formed during manufacture or prior to distribution to practitioners). In at least some embodiments, the at least one bend 420a and the at least one bend 420b are pre-defined such that the bends 420a and 420b are configured and arranged for insertion into bilateral intervertebral foramina from inside the epidural space. In at least some alternate embodiments, the at least one bend 420a and the at least one bend 420b are formable by practitioners prior to, or during, an implantation procedure.

In at least some embodiments, the at least one bend 420a and the at least one bend 420b are each no less than 50°, 60°, 70°, 80°, 90°, 100°, 110°, 120°, 130°, 140°, 150°, 160°, or more. In at least some embodiments, the at least one bend 420a and the at least one bend 420b are each no greater than 160°, 150°, 140°, 130°, 120°, 110°, 100°, 90°, 80°, 70°, 60°, 50°, or less. In at least some embodiments, the at least one bend 420a and the at least one bend 420b are each no less than 60° and no greater than 150°. In at least some embodiments, the at least one bend 420a and the at least one bend 420b are each no less than 80° and no greater than 130°.

In at least some embodiments, the at least one bend 420a and the at least one bend 420b are each configured and arranged to be straightened out upon application of force, yet also configured and arranged to reform upon removal of the force. For example, the at least one bend 420a and the at least one bend 420b may be configured and arranged to be straightened out when a stylet is inserted along one or more lumens defined within the stimulation arms 408a and 408b, or when the stimulation arms 408a and 408b are disposed in an introducer or insertion needle, or the like. In at least some embodiments, the curvature of the at least one bend 420a and the at least one bend 420b are each formed from one or more pre-shaped components of the stimulation arms 408a and 408b including, for example, pre-shaped insulation, or pre-shaped conductors, or both.

Figure 5A:
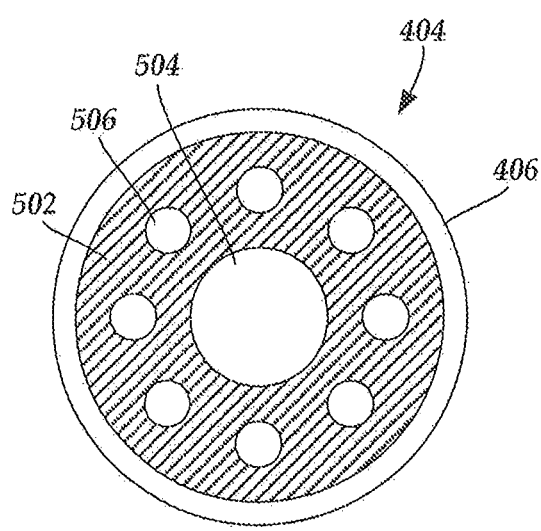
FIG. 5A is a transverse cross-sectional view of one embodiment of a portion of the major portion of the body of FIG. 4, the major portion including a multi-lumen conductor guide that defines a stylet lumen and a plurality of conductor lumens arranged around the stylet lumen, according to the invention.

Turning to FIG. 5A, in at least some embodiments the major portion of the lead body includes a multi-lumen conductor guide. FIG. 5A is a transverse cross-sectional view of one embodiment of the major portion 406 of the lead body 404. In at least some embodiments, the major portion 406 of the lead body 404 includes an elongated multi-lumen conductor guide 502 defining a single stylet lumen 504 and a plurality of conductor lumens, such as conductor lumen 506, disposed around the stylet lumen 504. The stylet lumen 504 may be configured and arranged to receive a stylet for stiffening the multi-armed lead and assisting in insertion and positioning of the multi-armed lead in the patient. The multi-lumen conductor guide 502 can define any suitable number of conductor lumens 506 for receiving any suitable number of conductors. In at least some embodiments, the multi-lumen conductor guide 502 defines eight conductor lumens 506. In at least some embodiments, the multi-lumen conductor guide 502 defines sixteen conductor lumens 506.

Figure 5B:
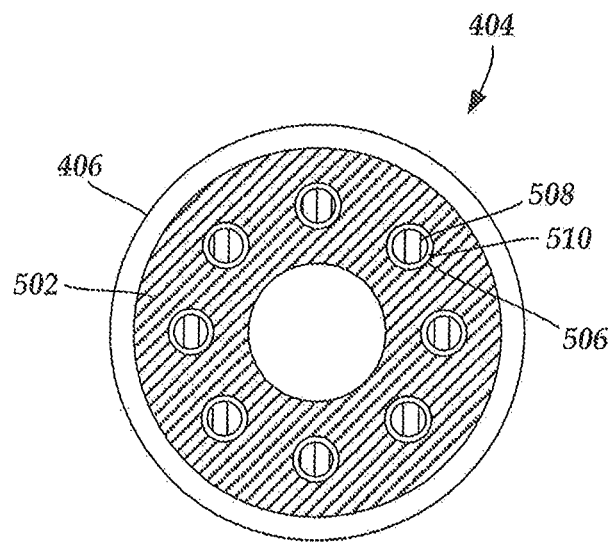
FIG. 5B is a transverse cross-sectional view of one embodiment of conductors disposed in each of a plurality of conductor lumens of the multi-lumen conductor guide of FIG. 5A, according to the invention.

FIG. 5B is a transverse cross-sectional view of one embodiment of conductors, such as conductor 508, disposed in conductor lumens 506. In at least some embodiments, insulation 510 is disposed around the conductors 508 to prevent short-circuiting of the conductors 508. The multi-lumen conductor guide 502 may extend an entire longitudinal length of the major portion 406 of the lead body 106. The conductors 508 can be formed from any conductor suitable for implantation. The conductor lumens 506 can be configured and arranged to each receive a single conductor 508 or a plurality of conductors 508. In embodiments that include conductors formed from conductive wires, it will be understood that an individual conductor 508 can be formed from conductive wires that are either single-filar or multi-filar.

Figure 6:
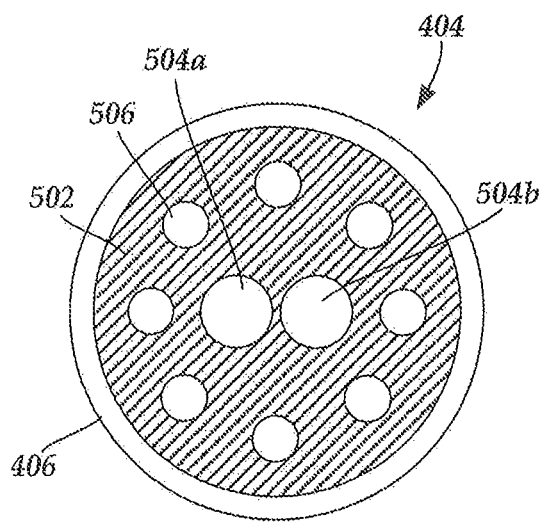
FIG. 6 is a transverse cross-sectional view of an alternate embodiment of a portion of the major portion of the body of FIG. 4, the major portion including a multi-lumen conductor guide that defines two stylet lumens and a plurality of conductor lumens arranged around the stylet lumens, according to the invention.

Turning to FIG. 6, in at least some embodiments the multi-lumen conductor guide defines a plurality of stylet lumens. FIG. 6 is a transverse cross-sectional view of another embodiment of a portion of the major portion 406. In at least some embodiments, the multi-lumen conductor guide 502 defines a plurality of stylet lumens 504a and 504b. In at least some embodiments, the number of stylet lumens 504 is equal to the number of stimulation arms 408a and 408b. In FIG. 6, the multi-lumen conductor guide 502 defines two stylet lumens 504a and 504b. As discussed below, it may be advantageous for the multi-lumen conductive guide 502 to define a plurality of stylet lumens 504 to enable a plurality of stylets to be simultaneously used to independently guide each of the stimulation arms 408a and 408b.

Figures 7A, 7B:
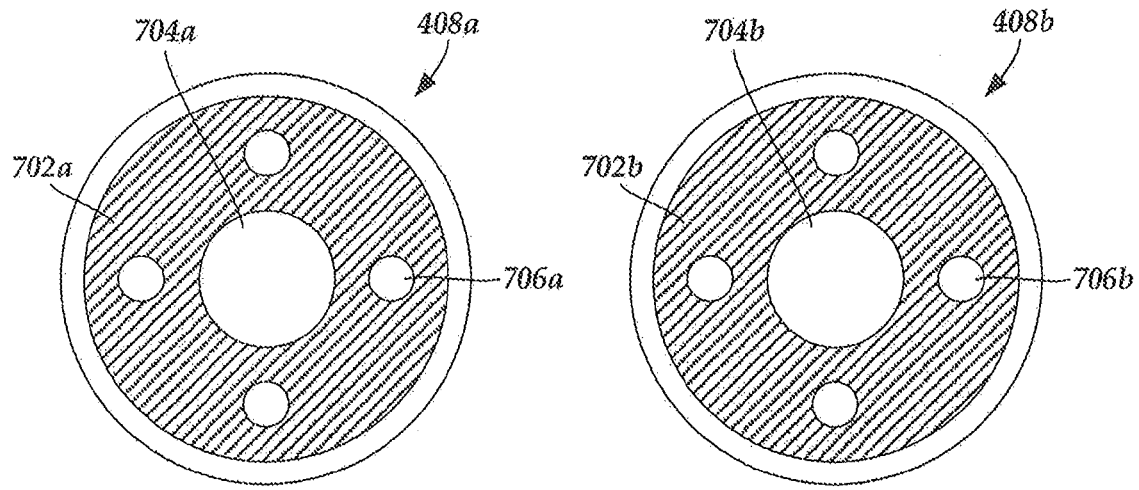
FIG. 7A is a schematic transverse cross-sectional view of one embodiment of a portion of one of the stimulation arms of the body of FIG. 4, the stimulation arm including a multi-lumen conductor guide that defines a stylet lumen and a plurality of conductor lumens arranged around the stylet lumen, according to the invention.
FIG. 7B is a schematic transverse cross-sectional view of one embodiment of a portion of one of the stimulation arms of the body of FIG. 4, the stimulation arm including a multi-lumen conductor guide that defines a stylet lumen and a plurality of conductor lumens arranged around the stylet lumen, according to the invention.

Turning to FIG. 7A, in at least some embodiments the stimulation arms include multi-lumen conductor guides. FIG. 7A is a transverse cross-sectional view of one embodiment of a portion of the stimulation arm 408a. The stimulation arm 408a includes a multi-lumen conductor guide 702a that defines a stylet lumen 704a and a plurality of conductor lumens, such as conductor lumen 706a, arranged around the stylet lumen 704a. The multi-lumen conductor guide 702a can define any suitable number of conductor lumens 706a. In at least some embodiments, the multi-lumen conductor guide 702a defines four conductor lumens 706a. In at least some embodiments, the multi-lumen conductor guide 702a defines eight conductor lumens 706a. In at least some embodiments, the multi-lumen conductor guide 702a defines half the number of conductor lumens 706a as does the multi-lumen conductor guide 502a.

FIG. 7B is a transverse cross-sectional view of one embodiment of a portion of the stimulation arm 408b. The stimulation arm 408b includes a multi-lumen conductor guide 702b that defines a stylet lumen 704b and a plurality of conductor lumens, such as conductor lumen 706b arranged around the stylet lumen 704b. The multi-lumen conductor guide 702b can define any suitable number of conductor lumens 706b. In at least some embodiments, the multi-lumen conductor guide 702b defines four conductor lumens 706b. In at least some embodiments, the multi-lumen conductor guide 702b defines eight conductor lumens 706b. In at least some embodiments, the multi-lumen conductor guide 702b defines half the number of conductor lumens 706b as does the multi-lumen conductor guide 502b. In at least some embodiments, the multi-lumen conductor guide 702b defines the same number of conductor lumens as does the multi-lumen conductor guide 502a.

Figure 8:
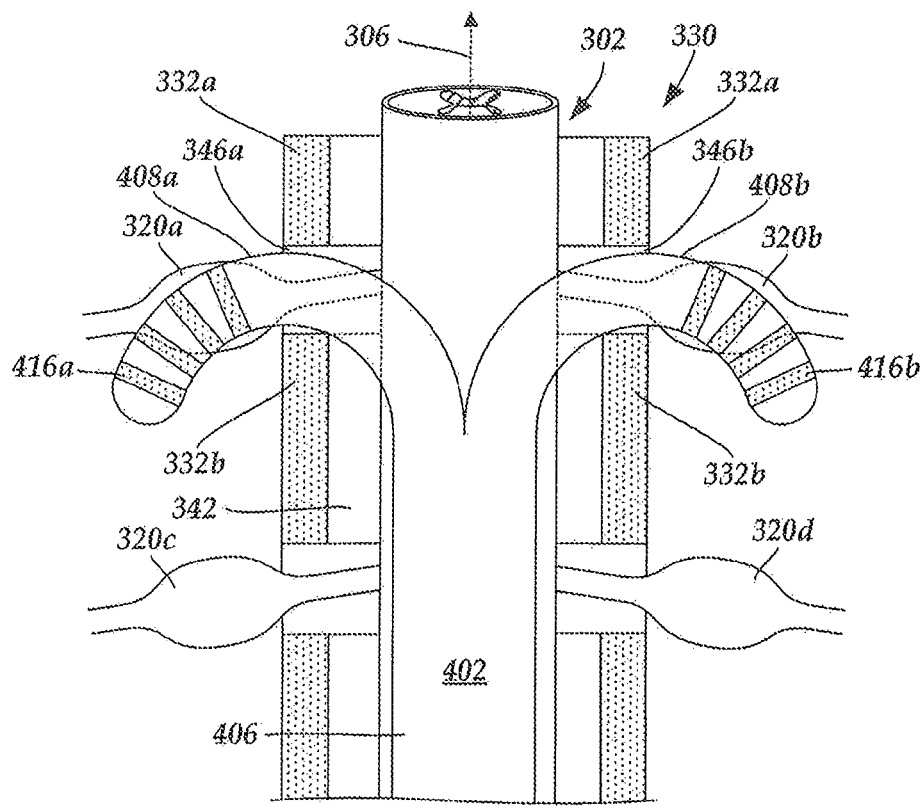
FIG. 8 is a schematic perspective view of the spinal cord of FIG. 3A disposed along a longitudinal transverse view of a portion of the vertebral column of FIG. 3B, where a side view of the distal end of the multi-armed lead of FIG. 4 is shown disposed along a portion of the spinal cord with electrodes of the multi-armed lead disposed along side of dorsal root ganglia extending from the spinal cord, according to the invention.

Turning to FIG. 8, once the multi-armed lead is inserted into the epidural space, the multi-armed lead may be advanced to the spinal level where bilateral DRG stimulation is desired and the stimulation arms 408a and 408b can be extended through the intervertebral foramen at that particular spinal level and positioned such that electrodes disposed along the stimulation arms are placed in operational proximity to the DRG.

FIG. 8 is a schematic perspective view of the spinal cord 302 disposed along a schematic longitudinal cross-sectional view of a portion of the vertebral column 330. The portion of the vertebral column 330 shown in FIG. 8 includes the vertebrae 332a and 332b and intervertebral foramina 346a and 346b defined between the vertebrae 332a and 332b on opposing sides of the vertebral column 330. The DRG 320a extends outward from the spinal cord 302 and through the intervertebral foramen 346a, and the DRG 320b extends outward from the spinal cord 302 and through the intervertebral foramen 346b. The DRG 320c and 320c are also shown in FIG. 8 extending from other intervertebral foramina.

The multi-armed lead 402 is shown disposed in the epidural space 342 along a portion of the midline 306 of the spinal cord 302. The stimulation arms 408a and 408b of the multi-armed lead 402 are extended out of the epidural space 342 between the vertebrae 332a and 332b. The stimulation arms 408a and 408b of the multi-armed lead 402 are extended out of the epidural space 342 via the intervertebral foramina 346a and 346b such that the stimulation arm 408a extends through the intervertebral foramen 346a and the stimulation arm 408b extends through the intervertebral foramen 346b.

The stimulation arm 408a is extended through the intervertebral foramen 346a such that the electrodes 416a disposed along the stimulation arm 408a are positioned in operational proximity to the DRG 320a. Similarly, the stimulation arm 408b is extended through the intervertebral foramen 346b such that the electrodes 416b disposed along the stimulation arm 408b are positioned in operational proximity to the DRG 320b.

Providing the multi-armed lead 402 with two stimulation arms 408a and 408b enables a single lead to simultaneously extend through the two intervertebral foramina 346a and 346b. In at least some embodiments, the stimulation arms 408a and 408b are configured and arranged to position the electrodes 416a and 416b such that the electrodes 416a and 416b are disposed in operational proximity to the DRG 320a and 320b, respectively, such that the electrodes 416a and 416b can simultaneously stimulate the two DRG 320a and 320b, if desired. In at least some embodiments, the bends 420a and 420b also function to anchor the multi-armed lead 402 to the vertebral column 330 and to prevent the electrodes 416a and 416b from migrating away from the DRG 320a and 320b, respectively, over time.

It will be understood that, alternately, the stimulation arms 408a and 408b can be implanted to concurrently stimulate two or more DRG located on the same side of a vertebral column (e.g., the DRG 320a and 320c, or 320b and 320d), or even two or more DRG at different spinal cord levels and on different sides of the vertebral column (e.g., the DRG 320a and 320d, or 320b and 320c).

It will also be understood that FIG. 8 is a schematic representation of the multi-armed lead 402 disposed in and around the vertebral column 330. The shapes and dimensions of the anatomical structures and at least some of the components of the multi-armed lead 402 are not be drawn to scale in FIG. 8, for clarity of illustration.

The multi-armed lead 402 can be implanted in any suitable manner. Several exemplary techniques are provided herein. In at least some embodiments, the multi-armed lead is advanced into the epidural space via a needle, such as an epidural needle. In at least some embodiments, the needle includes an obturator. Once the needle is advanced into the epidural space, the multi-armed lead is inserted into the needle and the distal end of the multi-armed lead is advanced to the epidural space. Once in the epidural space, the stimulation arms of the multi-armed lead are each guided within the epidural space and positioned in proximity to a different target stimulation location either in the epidural space or in proximity to the epidural space, such as two different DRG.

In at least some embodiments, one or more stylets are used to provide stiffness to the multi-armed lead to facilitate advancement of the multi-armed lead (e.g., along the needle, or within the epidural space, or both). For example, the one or more stylets can be inserted into the one or more stylet lumens of the multi-armed lead and used to guide the stimulation arms 408a and 408b of the multi-armed lead within the epidural space into and through the desired intervertebral foramina, such as the intervertebral foramina 346a and 346b, and in operational proximity to the target stimulation location (e.g., the DRG).

In at least some embodiments, when the distal end of the multi-armed lead is guided within the epidural space into and through the desired intervertebral foramina by a single stylet, the single stylet is disposed in the stylet lumen 504 of the major portion 406 of the lead body 404 (see e.g., FIG. 5A) and extended along the stylet lumen 504 and into the stylet lumen 704a of the stimulation arm 408a (see e.g., FIG. 7A). The stylet can then be used to guide that stimulation arm 408a into (and through) the intervertebral foramina 346a. Once the electrodes 416a of the stimulation arm 408a are in operational proximity to the target stimulation location (e.g., the DRG 320a), the stylet can be removed from the stylet lumen 704a and inserted into the stylet lumen 704b of the stimulation arm 408b (see e.g., FIG. 7B). The stylet can then be used to guide the stimulation arm 408b into (and through) the intervertebral foramina 346b and position the electrodes 416b in operational proximity to the target stimulation location (e.g., the DRG 320b).

In at least some other embodiments, when the distal end of the multi-armed lead is guided within the epidural space into and through the desired intervertebral foramina by two stylets, the two stylets are simultaneously disposed in the stylet lumen 504 of the major portion 406 of the lead body 404 (see e.g., FIG. 5A) with one of the two stylets extending into the stylet lumen 704a of the stimulation arm 408a (see e.g., FIG. 7A), and the other of the two stylets extending into the stylet lumen 704b of the stimulation arm 408b (see e.g., FIG. 7B).

Alternately, in at least some other embodiments when the distal end of the multi-armed lead is guided within the epidural space into and through the desired intervertebral foramina by two stylets, one of the two stylets is disposed in the stylet lumen 504a (see e.g., FIG. 6) of the major portion 406 of the lead body 404 and extended into the stylet lumen 704a of the stimulation arm 408a (see e.g., FIG. 7A), and the other of the two stylets is disposed in the stylet lumen 504b (see e.g., FIG. 6) of the major portion 406 of the lead body 404 and extended into the stylet lumen 704b of the stimulation arm 408b (see e.g., FIG. 7B).

It may be advantageous to use two stylets so that the two stimulation arms 408a and 408b may be simultaneously implanted, or sequentially implanted without needing to move a stylet between the stylet lumens 704a and 704b. Optionally, the one or more stylets can be steerable to facilitate guidance of the stimulation arms 408a and 408b into (and through) the desired intervertebral foramina, and in operational proximity to the target stimulation location (e.g., the DRG).

In at least some embodiments, the multi-armed lead is implanted into the patient using a combination of the needle and an introducer. For example, the needle may be advanced into the epidural space, as discussed above. Once the needle is in the epidural space, the obturator is removed and a guidewire is inserted into the needle and advanced into the epidural space. The needle is removed leaving the guidewire disposed in the epidural space.

A flexible introducer is disposed over the guidewire and advanced into the epidural space. The multi-armed lead is inserted into the introducer and advanced to the epidural space. When the stimulation arms are disposed in the introducer, the walls of the introducer exert a force against the stimulation arms that straighten the stimulation arms enough to be contained within the introducer.

In at least some embodiments, the introducer is disposed in the epidural space such that when the distal end of the multi-armed lead is extended outward from a distal end of the introducer, the stimulation arms are disposed along a region of the epidural space that is slightly beyond the spinal level of the intervertebral foramina through which the stimulation arms of the lead are desired to extend to reach the target stimulation location. When the stimulation arms are extended from the distal end of the introducer, the stimulation arms bend to reform the bends (420 in FIG. 4). In at least some embodiments, the outer walls of the epidural space exert a force against the stimulation arms that enable the stimulation arms to partially bend, but prevent the stimulation from fully bending. The introducer and multi-armed lead (with the partially-bent stimulation arms) are collectively pulled back and rotated (if needed) to position the distal tips of the stimulation arms into the desired intervertebral foramina.

The stimulation arms are then advanced through the intervertebral foramina to the target stimulation locations (e.g., the DRG). In at least some embodiments, one or more stylets may be used to facilitate advancement of the stimulation arms through the introducer, or through the intervertebral foramina, or both.

Figure 9:
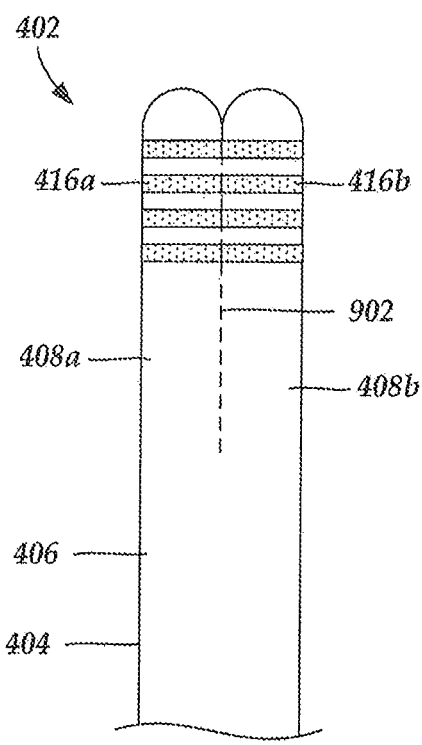
FIG. 9 is a schematic side view of the distal end of the multi-armed lead of FIG. 4, where stimulation arms of the multi-armed lead are coupled to one another along a perforated line, according to the invention.

In at least some embodiments, the stimulation arms may be coupled to one another (e.g., via one or more perforations) while being advanced into the epidural space. FIG. 9 is a schematic side view of the distal end of the multi-armed lead 402. The stimulation arms 408a and 408b are coupled to one another. In FIG. 9, the stimulation arms 408a and 408b are coupled to one another via a perforated line 902. It will be understood that the stimulation arms 408a and 408b can be coupled to one another in any suitable manner including, for example, adhesive, sutures, or the like or combinations thereof.

When the stimulation arms 408a and 408b are coupled together, movement of one of the stimulation arms 408a and 408b causes a corresponding movement of the other of the stimulation arms 408a and 408b. In at least some embodiments, when the stimulation arms 408a and 408b are coupled together the stimulation arms 408a and 408b do not bend independently from one another. In at least some embodiments, when the stimulation arms 408a and 408b are coupled together the portion of the lead body 404 that includes the major portion 406 is isodiametric with the portion of the lead body 404 that includes the stimulation arms 408a and 408b along at least one transverse axis.

When the stimulation arms are coupled to one another, the multi-armed lead can be advanced into the epidural space via either the needle or the introducer in combination with a guidewire. In at least some embodiments that include use of the guidewire, the guidewire is advanced into the epidural space and through one of the desired intervertebral foramina to one of the target stimulation locations (e.g., one of the DRG). The multi-armed lead is then advanced over the guidewire into the epidural space and out through a first intervertebral foramen to a first target stimulation location. A stylet is inserted into the multi-armed lead and used to uncouple the stimulation arms and reposition one of the stimulation arms out of the first intervertebral foramen and through a second intervertebral foramen to a second target stimulation location.

For example, in at least some embodiments the multi-armed lead 402 is advanced over the guidewire into the epidural space 342 and out through the intervertebral foramen 346a until the electrodes 416a of the stimulation arm 408a are positioned in operational proximity to the DRG 320a. A stylet is inserted into the stylet lumen (504 or 504b) of the major portion 406 of the multi-armed lead 402 and into the stylet lumen 704b of the stimulation arm 408b. The stylet is then used to uncouple (e.g., peel apart) the stimulation arms 408a and 408b such that the electrodes 416a of the stimulation arm 408a remain in operational proximity to the DRG 320a. The stylet is used to reposition the stimulation arm 408b out of the first intervertebral foramen 346a, back into the epidural space 342, and out through the intervertebral foramen 346b until the electrodes 416b of the stimulation arm 408b are positioned in operational proximity to the DRG 320b.

Figure 10:
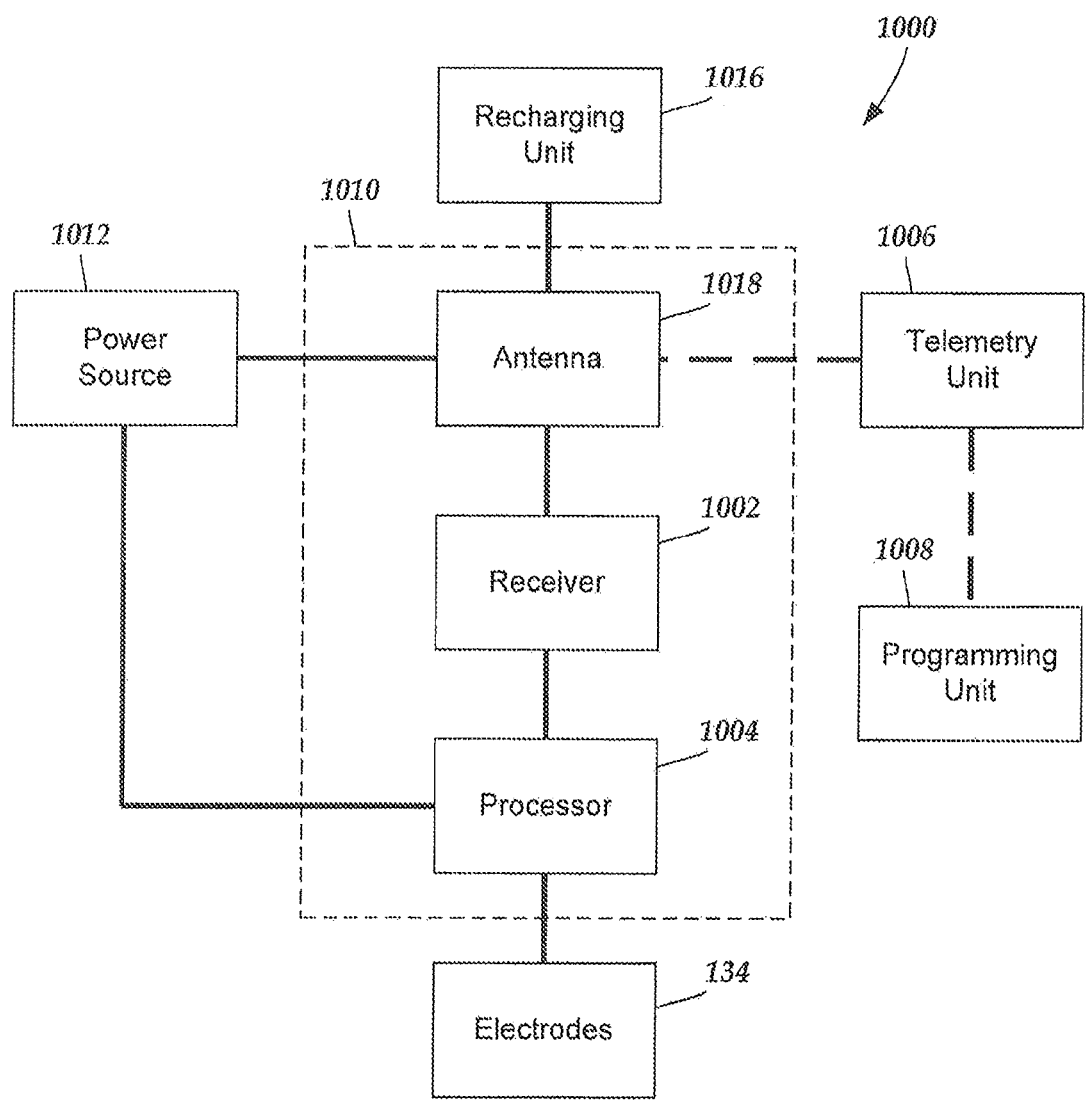
FIG. 10 is a schematic overview of one embodiment of components of an electrical stimulation system, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office.

The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for implanting an electrical stimulation lead into a patient, the method comprising:
   advancing a distal end portion of a multi-armed lead into an epidural space of the patient, the multi-armed lead comprising a main body portion, a first stimulation arm extending from a distal end portion of the main body portion, and a second stimulation arm extending from the distal end portion of the main body portion;
   advancing the first stimulation arm through a first intervertebral foramen from inside the epidural space; and
   advancing the second stimulation arm through a second intervertebral foramen from inside the epidural space.

2. The method of claim 1, wherein the first intervertebral foramen and the second intervertebral foramen are disposed at a same spinal cord level.

3. The method of claim 1, wherein the first intervertebral foramen and the second intervertebral foramen are disposed at different spinal cord levels.

4. The method of claim 1, wherein the first intervertebral foramen and the second intervertebral foramen are disposed along opposing sides of the patient's vertebral column.

5. The method of claim 1, wherein the first intervertebral foramen and the second intervertebral foramen are disposed along the same side of the patient's vertebral column.

6. The method of claim 1, wherein guiding the first stimulation arm into and through the first intervertebral foramen from inside the epidural space comprises inserting a first stylet into the first stimulation arm and using the first stylet to guide the first stimulation arm into and through the first intervertebral foramen.

7. The method of claim 6, wherein guiding the second stimulation arm into and through the second intervertebral foramen from inside the epidural space comprises inserting the first stylet into the second stimulation arm and using the first stylet to guide the second stimulation arm into and through the second intervertebral foramen.

8. The method of claim 6, wherein guiding the second stimulation arm into and through the second intervertebral foramen from inside the epidural space comprises inserting a second stylet into the second stimulation arm and using the second stylet to guide the second stimulation arm into and through the second intervertebral foramen.

9. The method of claim 8, wherein the first stylet and the second stylet are simultaneously disposed in the multi-armed lead during at least a portion of the implantation of the multi-armed lead into the patient.

10. The method of claim 1, wherein advancing a distal end portion of a multi-armed lead into an epidural space of the patient comprises advancing the distal end portion of the multi-armed lead into the epidural space of the patient while the first stimulation arm is coupled to the second stimulation arm.

11. The method of claim 10, further comprising uncoupling the second stimulation arm from the first stimulation arm subsequent to advancing the distal end portion of the multi-armed lead into the epidural space of the patient.

12. The method of claim 1, further comprising
    anchoring the first stimulation arm to the first intervertebral foramen using a pre-defined bend formed along the first stimulation arm; and
    anchoring the second stimulation arm to the second intervertebral foramen using a pre-defined bend formed along the second stimulation arm.

13. An implantable lead for providing electrical stimulation to a patient, the lead comprising:
    a lead body having a proximal end portion, a distal end portion, and a longitudinal length, the lead body comprising
        a main body portion having a proximal end portion, a distal end portion, and a longitudinal length,
        a first stimulation arm extending from the distal end portion of the main body portion,
        a plurality of first electrodes disposed along the first stimulation arm,
        a second stimulation arm extending from the distal end portion of the main body portion, and
        a plurality of second electrodes disposed along the second stimulation arm,
        wherein the first stimulation arm is configured and arranged for extending through a first intervertebral foramen when the main body portion is disposed in the epidural space,
        wherein the second stimulation arm is configured and arranged for extending through a second intervertebral foramen when the main body portion is disposed in an epidural space;
    a plurality of terminals disposed along the proximal end portion of the main body portion; and
    a plurality of conductors electrically coupling the plurality of terminals to the plurality of first electrodes and to the plurality of second electrodes.

14. The lead of claim 13, wherein a first pre-defined bend is formed along the first stimulation arm and a second pre-defined bend is formed along the second stimulation arm.

15. The lead of claim 14, wherein the first pre-defined bend is oriented in an opposite direction from the second pre-defined bend.

16. The lead of claim 14, wherein the first pre-defined bend is symmetric with the second pre-defined bend along an axis of symmetry extending along the longitudinal length of the major body portion.

17. The lead of claim 14, wherein the first pre-defined bend and the second pre-defined bend are each configured and arranged to straighten upon application of force and to reform upon removal of the applied force.

18. The lead of claim 14, wherein the first pre-defined bend and the second pre-defined bend are each no less than 50° and no greater than 160°.

19. The lead of claim 13, wherein the first stimulation arm and the second stimulation arm are configured and arranged for being removably coupled to one another during insertion of the lead into the patient.

20. An electrical stimulating system comprising:
the lead of claim 13;
a control module electrically coupled to the plurality of first electrodes of the first stimulation arm of the lead and to the plurality of second electrodes of the second stimulation arm of the lead, the control module comprising
a housing, and
an electronic subassembly disposed in the housing; and
a connector assembly for receiving the lead, the connector assembly comprising
a connector housing defining at least one port configured and arranged for receiving the major body portion of the lead, and
a plurality of connector contacts disposed in the connector housing, the plurality of connector contacts configured and arranged to couple to the plurality of terminals disposed along the major body portion when the major body portion is received by the at least one port.

* * * * *